United States Patent
Maerz et al.

(10) Patent No.: US 10,138,180 B2
(45) Date of Patent: Nov. 27, 2018

(54) PRODUCTION OF STYRENE

(71) Applicant: BADGER LICENSING LLC, Boston, MA (US)

(72) Inventors: Brian Maerz, Chelmsford, MA (US); Vijay Nanda, Houston, TX (US); Maruti Bhandarkar, Kingwood, TX (US); Matthew Vincent, Baytown, TX (US)

(73) Assignee: BADGER LICENSING LLC, Boston, MA (US)

( * ) Notice: Subject to any disclaimer, the term of this patent is extended or adjusted under 35 U.S.C. 154(b) by 0 days.

(21) Appl. No.: 14/646,852

(22) PCT Filed: Nov. 27, 2012

(86) PCT No.: PCT/US2012/066621
§ 371 (c)(1),
(2) Date: May 22, 2015

(87) PCT Pub. No.: WO2014/084810
PCT Pub. Date: Jun. 5, 2014

(65) Prior Publication Data
US 2015/0321973 A1    Nov. 12, 2015

(51) Int. Cl.
C07C 2/66 (2006.01)
C07C 6/12 (2006.01)
C07C 5/327 (2006.01)
C07C 5/333 (2006.01)
C07C 6/06 (2006.01)
C07C 7/12 (2006.01)
C07C 7/13 (2006.01)

(52) U.S. Cl.
CPC ............. *C07C 5/3332* (2013.01); *C07C 2/66* (2013.01); *C07C 5/333* (2013.01); *C07C 6/06* (2013.01); *C07C 7/12* (2013.01); *C07C 7/13* (2013.01); *C07C 2521/04* (2013.01); *C07C 2523/745* (2013.01); *C07C 2523/78* (2013.01); *C07C 2523/847* (2013.01); *C07C 2523/86* (2013.01); *C07C 2523/881* (2013.01); *C07C 2529/06* (2013.01); *C07C 2529/08* (2013.01); *C07C 2529/18* (2013.01); *C07C 2529/40* (2013.01); *C07C 2529/65* (2013.01); *C07C 2529/70* (2013.01)

(58) Field of Classification Search
CPC .............. C07C 2/66; C07C 6/12; C07C 5/327
USPC ................. 585/323, 440, 470, 823
See application file for complete search history.

(56) References Cited

U.S. PATENT DOCUMENTS

| | | |
|---|---|---|
| 4,009,217 A | 2/1977 | Uitti |
| 6,297,417 B1 | 10/2001 | Samson et al. |
| 6,894,201 B1 * | 5/2005 | Schmidt ............. C07C 2/66 585/448 |
| 2005/0288539 A1 | 12/2005 | Jeanneret et al. |
| 2009/0149685 A1 | 6/2009 | Butler et al. |
| 2009/0326291 A1 * | 12/2009 | Jan ............. C07C 2/66 585/270 |
| 2010/0268008 A1 | 10/2010 | Hwang et al. |
| 2013/0338416 A1 * | 12/2013 | Riley ............. C07C 7/12 585/323 |

FOREIGN PATENT DOCUMENTS

WO    20090046977 A1    4/2009

OTHER PUBLICATIONS

International Preliminary Report on Patentability mailed in corresponding PCT/US2012/066621 dated Mar. 9, 2015.

\* cited by examiner

*Primary Examiner* — Thuan D Dang
(74) *Attorney, Agent, or Firm* — Roberts Mlotkowski Safran Cole & Calderon P.C.

(57) ABSTRACT

In a process for producing styrene, benzene is alkylated with ethylene to produce ethylbenzene and at least some of the ethylbenzene is dehydrogenated to produce styrene, together with benzene and toluene as by-products. At least part of the benzene by-product is passed through a bed of an adsorbent comprising at least one of an acidic clay, alumina, an acidic ion exchange resin and an acidic molecular sieve to remove basic nitrogenous impurities therefrom and produce a purified benzene by-product, which is then recycled to the alkylation step.

8 Claims, No Drawings

PRODUCTION OF STYRENE

CROSS-REFERENCE TO RELATED APPLICATIONS

The present application is a U.S. National Phase of PCT/US2012/066621 filed on Nov. 27, 2012. The disclosure of the PCT Application is hereby incorporated by reference into the present Application.

FIELD

This invention relates to a process for the production of styrene.

BACKGROUND

Styrene is an important monomer used in the manufacture of many plastics and is commonly produced in a two-step process. In the first step, benzene is alkylated with an ethylating agent, such as ethylene, over a molecular sieve catalyst to form ethylbenzene (EB) and polyethylbenzenes (PEBs), the latter comprising diethylbenzenes (DEBs), triethylbenzenes (TEBs), and heavier aromatic compounds. To maximize EB formation, the light PEBs (DEBs and TEBs) are usually transalkylated with benzene, again over a molecular sieve catalyst to form more EB. Both the alkylation and transalkylation effluents flow to a distillation train, which recovers unreacted benzene, EB, and the light PEBs as distillates in three distillation columns in series.

In the second step, the EB is dehydrogenated to styrene over an iron catalyst in the presence of steam, which supplies the sensible heat needed for the endothermic reaction and which reacts with coke deposited on the catalyst to form carbon oxides, mainly carbon dioxide. Benzene and toluene are by-products of the dehydrogenation reaction and so the crude styrene effluent leaving the reaction section of styrene plant comprises benzene, toluene, unreacted EB, styrene monomer, steam and small amounts of heavier aromatic compounds. Crude styrene condenses along with the steam in a final reactor effluent cooling step, forming separate aqueous and aromatic hydrocarbon phases, which are separated to recover an aromatic hydrocarbon phase saturated with water.

Acidity due to carbon dioxide dissolved in the aqueous phase of the crude styrene effluent can cause corrosion in downstream equipment and can hinder the separation of the organic and aqueous phases. Thus, in most plants, a corrosion inhibitor (a solution containing one or more amines or other basic nitrogen compounds) is added upstream of the condensation step to control corrosion. These compounds tend to partition with the aqueous phase in the separator. However, although these compounds typically boil at a higher temperature than the styrene monomer, they may break down to lighter nitrogen-containing compounds in the dehydrogenation reactor if a portion of the aqueous phase is used to generate the steam required in dehydrogenation.

After recovery of the crude styrene, the benzene/toluene ("B/T") fraction is separated from ethylbenzene and heavier aromatics by distillation. The B/T fraction may also be recovered from an ethylbenzene-and-lighter fraction distilled from crude styrene in a preceding distillation column. In either configuration, water, $CO_2$, and any light nitrogen-containing compounds present in the crude styrene effluent will distill with the B/T fraction, and a portion of these compounds will be present in B/T byproduct. Water and $CO_2$ are present in the column overhead, again raising corrosion issues, so some plants inject additional corrosion inhibitor into the overhead. A separate water phase forms in the overhead condensing equipment and, although most of the amine injected will partition with the water phase, some will be present in the B/T byproduct.

As a result, the B/T fraction recovered from the dehydrogenation effluent typically contains high levels (in excess of 2 ppm) of basic nitrogen impurities, typically 10 to 100 times the concentration of nitrogen-containing compounds in the fresh benzene feed to the alkylation process. Although it would appear to be desirable to recycle at least the benzene in the B/T fraction to the alkylation reactor, the high concentration of nitrogen impurities in such a benzene recycle stream presents a serious challenge. Thus the active acid sites on the molecular sieve catalyst used in the alkylation reactor are titrated by basic compounds, such as the nitrogen impurities in the benzene byproduct, reducing the activity of the catalyst. In fact, acidic adsorbents are typically used to reduce even the relatively low levels of nitrogenous impurities present in the fresh benzene feed before this is allowed to contact the alkylation catalyst. There has therefore been significant disincentive in the art against recycling the benzene byproduct from the styrene plant back to the EB alkylation reactor.

Thus, U.S. Published Patent Application No. 2005/0288539 discloses a process for producing styrene in which the by-product benzene recovered from the EB dehydrogenation reaction is recycled to the transalkylation reactor rather than the alkylation reactor. The purported advantages of this process are that the adverse effect of this recycle stream is less on the transalkylation catalyst than on the alkylation catalyst and the transalkylation catalyst typically costs less than, and is cheaper to replace, than the alkylation catalyst.

U.S. Published Patent Application No. 2009/0149685 discloses a method for reducing alkylation catalyst poisoning, wherein the method comprises providing a dehydrogenation system including a dehydrogenation reactor and a separation system, wherein the separation system includes a first column and a second column, introducing an alkyl aromatic hydrocarbon into the dehydrogenation reactor, contacting the alkyl aromatic hydrocarbon with a dehydrogenation catalyst disposed within the dehydrogenation reactor to form a dehydrogenation output stream comprising a vinyl aromatic hydrocarbon, passing at least a portion of the dehydrogenation output stream to first column, recovering a first overhead fraction including benzene and a first bottoms fraction from the first column, passing at least a portion of the benzene from the first column to an alkylation system including an alkylation catalyst, passing the first bottoms fraction from the first column to the second column, recovering a second overhead fraction and a second bottoms fraction from the second column, withdrawing offtest from effluent streams selected from the dehydrogenation output stream, the first bottoms fraction, the second bottoms fraction and combinations thereof to form withdrawn offtest and introducing the withdrawn offtest into the separation system downstream from the first column.

According to the present invention, it has now been found that, by passage of at least the benzene by-product of a styrene plant through a dedicated adsorbent bed comprising at least one of acidic clay, alumina, an acidic ion exchange resin and an acidic molecular sieve, poisons, such as basic nitrogen compounds, can be effectively removed from the benzene by-product. The resultant purified benzene stream has a sufficiently low concentration of (typically less than 50 ppbw) of basic nitrogen compounds that the stream can be advantageously recycled to the EB alkylation and/or transalkylation reactor.

SUMMARY

In one aspect, the invention resides in a process for producing styrene, the process comprising:
(a) alkylating benzene with ethylene to produce ethylbenzene;
(b) dehydrogenating at least some of the ethylbenzene from (a) to produce styrene, together with benzene and toluene as by-products;
(c) passing at least part of the benzene by-product from (b) through a bed of an adsorbent comprising at least one of an acidic clay, alumina, an acidic ion exchange resin and an acidic molecular sieve to remove basic nitrogenous impurities therefrom and produce a purified benzene by-product; and
(d) recycling the purified benzene by-product to the alkylating (a).

In a further aspect, the invention resides in a process for producing styrene, the process comprising:
(a) alkylating benzene with ethylene to produce ethylbenzene and polyethylated benzenes;
(b) transalkylating at least some of the polyethylated benzenes from (a) with benzene to produce additional ethylbenzene;
(c) dehydrogenating at least some of the ethylbenzene from (a) and (b) to produce styrene, together with benzene and toluene as by-products;
(d) passing at least part of the benzene by-product from (c) through a bed of an adsorbent comprising at least one of an acidic clay, alumina, an acidic ion exchange resin and an acidic molecular sieve to remove basic nitrogenous impurities therefrom and produce a purified benzene by-product; and
(e) recycling the purified benzene by-product to the alkylating (a) and/or the transalkylating (b).

Generally, the dehydrogenating is conducted in the presence of steam and the benzene by-product contains water. In one embodiment, the adsorbent comprises an acidic clay and/or an acidic ion exchange resin and the water-containing benzene by-product is passed through the bed of adsorbent. In another embodiment, the benzene by-product is dried before passage through the bed of adsorbent.

Typically, a fraction containing both of the benzene and toluene by-products is separated from the dehydrogenation effluent. In one embodiment, part or all of this fraction is passed through the bed of adsorbent without an intermediate fractionation step. In another embodiment, part or all of this fraction is distilled to produce a benzene-rich fraction and a toluene-rich fraction and only the benzene-rich fraction is passed through the bed of adsorbent.

In one embodiment, the benzene by-product produced by the dehydrogenating contains in excess of 2 ppm of basic nitrogen compounds and the purified benzene by-product contains less than 50 ppb of basic nitrogen compounds.

Generally, the alkylating (a) is conducted in the presence of a molecular sieve catalyst and the purified benzene by-product is recycled to the alkylating step. Typically, the molecular sieve employed in the alkylation catalyst is selected from the group consisting of ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, zeolite Y, Ultrastable Y (USY), Dealuminized Y (Deal Y), mordenite, MCM-22, PSH-3, SSZ-25, ERB-1, ITQ-1, ITQ-2, MCM-36, MCM-49, MCM-56, and UZM-8.

DETAILED DESCRIPTION OF THE EMBODIMENTS

Described herein is a two-stage process for the production of styrene involving, in a first stage, the alkylation of benzene with ethylene in the presence of a molecular sieve catalyst to produce ethylbenzene followed, in a second stage, by dehydrogenation of the resultant ethylbenzene to produce the desired styrene together with benzene as a by-product. The present process provides, a simple and efficient system for separating and recycling the benzene by-product of the dehydrogenation reaction back to the alkylation step without exposing the molecular sieve alkylation catalyst to dangerous levels of basic nitrogen impurities generated during styrene production.

Production of Ethylbenzene

In the present process, benzene is initially alkylated with ethylene in the presence of a molecular sieve alkylation catalyst. Generally, the molecular sieve employed in the alkylation catalyst is a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No.

6,756,030), and mixtures thereof. Preferably, the molecular sieve is selected from (a) MCM-49, (b) MCM-56 and (c) isotypes of MCM-49 and MCM-56, such as ITQ-2.

In other embodiments, a suitable zeolite for use in the alkylation catalyst may comprise a medium pore molecular sieve having a Constraint Index of 2-12 (as defined in U.S. Pat. No. 4,016,218), including ZSM-5, ZSM-11, ZSM-12, ZSM-22, ZSM-23, ZSM-35, and ZSM-48. ZSM-5 is described in detail in U.S. Pat. No. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference.

In still other embodiments, a suitable zeolite for use in the alkylation catalyst may comprise a large pore molecular sieve having a Constraint Index of less than 2. Suitable large pore molecular sieves include zeolite beta, zeolite Y, Ultrastable Y (USY), Dealuminized Y (Deal Y), mordenite, ZSM-3, ZSM-4, ZSM-18, a MCM-22 family material, and ZSM-20. Zeolite ZSM-14 is described in U.S. Pat. No. 3,923,636. Zeolite ZSM-20 is described in U.S. Pat. No. 3,972,983. Zeolite beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

The zeolite or molecular sieve present in the alkylation catalyst will usually be an aluminosilicate having an alpha value in the range of from about 100 to about 1000. The alpha value is a measure of molecular sieve acidic functionality and is described together with details of its measurement in U.S. Pat. No. 4,016,218 and in J. Catalysis, Vol. VI, pp. 278-287 (1966) and reference is made to these for such details. Higher alpha values correspond with a more active cracking catalyst.

The molecular sieves described above may be used in the alkylation catalyst in unbound form but generally will be combined with a binder material resistant to the temperature and other conditions employed in the process. Examples of suitable binder material include clays, alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The molecular sieve may also be composited with zeolitic material such as the zeolitic materials which are disclosed in U.S. Pat. No. 5,993,642, which is hereby incorporated by reference. The relative proportions of molecular sieve and binder material can vary widely with the molecular sieve content ranging from between about 1 to about 99 percent by weight, more preferably between about 10 to 70 percent by weight, and still more preferably between about 40 to about 70 percent by weight of the total catalyst.

The alkylation of benzene with ethylene is normally carried out in one or more fixed bed reactors under alkylation conditions such that the benzene feed is at least partially in the liquid phase. Typical alkylation conditions include a temperature of from about 120 to 300° C., preferably, a temperature of from about 150 to 260° C., a pressure of 689 to 4601 kPa-a, preferably, a pressure of 1500 to 4137 kPa-a, a WHSV of 0.1 to 10 $hr^{-1}$, preferably 0.2 to 2 $hr^{-1}$, more preferably 0.5 to 1 $hr^{-1}$, based on ethylene feed, and a molar ratio of benzene to ethylene from about 1 to about 100, preferably from about 20 to about 80.

The product of the alkylation reaction comprises ethylbenzene (EB), together with some polyalkylated species, particularly diethylbenzenes (DEBs) and triethylbenzenes (TEBs), as well as unreacted benzene and some hydrocarbons heavier than TEB. The process is normally conducted so that all the ethylene feed is consumed in the reaction.

The alkylation product is fed to a distillation train, which includes a benzene column for removing unreacted benzene for recycle to the alkylation process; an EB column for recovering the ethylbenzene product and a PEB column for separating the DEBs and TEBs from the heavier hydrocarbons.

To maximize EB production, the DEBs and TEBs recovered in the PEB column are generally fed to one or more fixed bed transalkylation reactors where the polyethylbenzenes are reacted with further benzene in the presence of a molecular sieve catalyst to produce additional ethylbenzene. The transalkylation catalyst may comprise a medium pore molecular sieve having a Constraint Index of 2-12 (as defined in U.S. Pat. No. 4,016,218), including ZSM-5, ZSM-11, ZSM-12, ZSM-22, ZSM-23, ZSM-35, and ZSM-48. Alternatively, the transalkylation catalyst may comprise a large pore molecular sieve having a Constraint Index of less than 2, such as zeolite beta, an MCM-22 family material, zeolite Y, Ultrastable Y (USY), Dealuminized Y (Deal Y), mordenite, ZSM-3, ZSM-4, ZSM-18, ZSM-20. or any combination thereof. The transalkylation reaction generally take place under at least partially in liquid phase conditions, including a temperature of from about 100 to about 300° C., a pressure of 696 to 4137 kPa-a, a WHSV based on the weight of the polyalkylated aromatic compound(s) feed to the transalkylation reaction of from about 0.5 to about 100 $hr^{-1}$ and a molar ratio of benzene to polyalkylated aromatic compound(s) of from 1:1 to 30:1, preferably, 1:1 to 10:1, more preferably, 1:1 to 5:1.

The product of the transalkylation reaction comprises ethylbenzene, PEBs and other heavy hydrocarbons normally together with unreacted benzene. The product is mixed with the reaction effluent from the alkylation reactor and supplied to the distillation train for recovery of the ethylbenzene.

Ethylbenzene Dehydrogenation to Styrene

The ethylbenzene recovered from the EB column is fed to one or more series-connected dehydrogenation reactors each containing a dehydrogenation catalyst. Generally, the dehydrogenation catalyst comprises iron oxide, optionally together with one or more promoters, such as, for example, chromium oxide, cesium oxide, molybdenum oxide, magnesium oxide, aluminum oxide, vanadium oxide, calcium oxide, and the like. Conditions in the dehydrogenation reactors are sufficient to convert the ethylbenzene to styrene and generally include a temperature of about 530 to about 650° C., a pressure of about 35 to about 100 kPa-a and a hydrogen to hydrocarbon mole ratio of about 5 to about 10. Typically, steam is also supplied to the dehydrogenation reactors to provide heat to the endothermic reaction and to convert coke deposited on the catalyst to carbon oxides, particularly carbon dioxide.

The effluent from the dehydrogenation reactors comprises styrene, unreacted ethylbenzene, steam, $CO_x$ and a variety of by-products, including benzene and toluene as well as heavier aromatic compounds. On leaving the dehydrogenation section, the effluent is cooled so as to condense the styrene and steam and separate a styrene-containing aromatic phase and an aqueous phase from the effluent. The carbon dioxide generated by the decoking reaction dissolves in and separates with the aqueous phase potentially rendering the latter acidic, which could cause corrosion in downstream equipment as well as hinder the separation of the organic and aqueous phases. Thus, a corrosion inhibitor (a solution containing one or more amines or other basic organic nitrogen compounds) is generally added upstream of the condensation step to reduce or eliminate the acidity of the aqueous phase.

After removal from the dehydrogenation effluent, the aromatic and liquid phases are passed to a liquid/liquid separator where the crude styrene is recovered leaving an aqueous fraction which is recycled to the dehydrogenation reactor for steam generation. The basic nitrogen compounds added to reduce corrosion preferentially partition with the aqueous fraction in the separator and tend break down to lighter nitrogen-containing compounds when the aqueous phase is recycled to the dehydrogenation reactor. As a result, the entire dehydrogenation effluent typically contains relatively high levels (in excess of 1 ppm by weight) of basic nitrogen impurities.

After recovery of the crude styrene, the benzene/toluene ("B/T") fraction is separated from the unreacted ethylbenzene and heavier aromatics in the dehydrogenation effluent by distillation. Water, $CO_2$, and any light nitrogen-containing compounds present in the effluent distill with the B/T overhead fraction, and so a portion of these compounds are always present in B/T byproduct. In addition, the presence of water and $CO_2$ in the B/T overhead stream again raises corrosion issues, so that additional amine corrosion inhibitors are conveniently added to the overhead. The B/T overhead stream is then passed through a condenser to remove most of the water and, although the additional amine tends to partition with the water phase, some is retained in the B/T byproduct. Thus, the B/T fraction recovered from the dehydrogenation effluent typically contains in excess of 2 ppm by weight of basic nitrogen impurities, which is typically 10 to 100 times the concentration of nitrogen-containing compounds in the fresh benzene feed to the alkylation process. In addition, the B/T fraction typically contains in excess of 200 ppm by weight of water.

In the present process, the B/T byproduct, either with or without prior fractionation to remove the toluene, is passed through one or more beds of adsorbent effective to reduce the level of basic nitrogen compounds to sufficiently low levels (typically less than 50 ppbw) that at least the benzene fraction can be recycled to the EB alkylation reactor. Suitable adsorbents include acidic clays, alumina, acidic ion exchange resins, acidic molecular sieves and mixtures thereof. Depending on the adsorbent employed it may be desirable to dry the B/T byproduct or the benzene fraction thereof before passage through the adsorbent bed(s). For example, it is found that acidic clays are generally effective to provide the required reduction of basic nitrogen impurities even when the B/T byproduct or the benzene fraction thereof is saturated with water. However, molecular sieve adsorbents, such as mole sieve 13X, are typically hygroscopic so that water adsorption will compete with removal of nitrogenous impurities. Thus, with molecular sieve adsorbents, it is found to be preferable to dry the B/T byproduct or the benzene fraction thereof before nitrogen removal.

In one embodiment, the B/T byproduct is fractionated to recover the benzene fraction and, after passage through the adsorbent bed(s), the benzene fraction is recycled to the benzene alkylation reaction and/or the PEB transalkylation reaction.

The invention will now be more particularly described with reference to the Examples.

EXAMPLE 1 (COMPARATIVE)

A clean, dry benzene feed (>99% purity) is fed to a fixed-bed alkylation reactor equipped with a multipoint thermocouple so that the internal bed temperature can be measured at various bed depths. With the bed at an initial, temperature of 200° C., a measured amount of ethylene is added to the bed using a mass flow meter. Since the ethylation of benzene is an exothermic reaction, the temperature in the bed rises as the reaction progresses and is measured by the thermocouple. The percentage of the total temperature rise across the catalyst bed, being proportional to the extent of reaction, is used to gauge catalyst aging. With the clean benzene feed the percentage temperature rise remains substantially constant indicating that the catalyst is stable.

An untreated benzene fraction obtained as the byproduct of an ethylbenzene dehydrogenation process is then added to the benzene feed and the percentage temperature rise rapidly decreases showing that the catalyst is aging.

EXAMPLE 2

The process of Example 1 is repeated, but in this case the benzene fraction from the ethylbenzene dehydrogenation process is initially dried by azeotropic distillation or by passing through a bed of activated alumina or other material with an affinity for water and is then passed through a bed of mole sieve 13X before being fed to the alkylation reactor. The percentage temperature rise remains substantially constant after the addition of the treated benzene indicating minimal catalyst aging.

EXAMPLE 3

The process of Example 1 is repeated but in this case the benzene fraction from the ethylbenzene dehydrogenation process is passed through a bed of acid-activated clay, without an initial drying step, before being fed to the alkylation reactor. The percentage temperature rise again remains substantially constant after the addition of the treated benzene indicating minimal catalyst aging.

EXAMPLE 4

The process of Example 2 is repeated but with the adsorbent bed comprising a mixture of mole sieve 13X and acid-activated clay. Again the percentage temperature rise remains substantially constant after the addition of the treated benzene indicating minimal catalyst aging.

EXAMPLE 5

The process of Example 2 is repeated but with the adsorbent bed comprising a Amberlyst 15DRY ion exchange resin. Again the percentage temperature rise remains substantially constant after the addition of the treated benzene indicating minimal catalyst aging.

The invention claimed is:

1. A process for producing styrene, the process comprising:
    (a) alkylating benzene with ethylene to produce ethylbenzene;
    (b) dehydrogenating at least part of the ethylbenzene from (a) to produce a dehydrogenation effluent comprising styrene, together with benzene and toluene as by-products;
    (c) separating a fraction containing benzene, toluene and water from the dehydrogenation effluent without prior fractionation to remove the toluene, wherein said fraction contains in excess of 2 ppm by weight of basic nitrogen impurities;
    (d) passing at least part of the benzene, toluene and water-containing fraction through a bed of an adsorbent comprising at least one of an acidic clay, and an acidic ion exchange resin to remove basic nitrogenous impurities therefrom and produce a purified benzene, toluene and water-containing fraction containing less than 50 ppb by weight of basic nitrogen impurities; and
    (e) recycling a purified benzene fraction to the alkylating (a).

2. The process of claim 1, wherein the dehydrogenating is conducted in the presence of steam.

3. The process of claim 2, wherein the adsorbent comprises an acidic clay and the benzene, toluene and water-containing fraction is passed through the bed of adsorbent.

4. The process of claim 1, wherein the alkylating (a) is conducted in the presence of a zeolite catalyst.

5. The process of claim 4, wherein the zeolite is selected from the group consisting of ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, zeolite Y, Ultrastable Y (USY), Dealuminized Y (Deal Y), mordenite, MCM-22, PSH-3, SSZ-25, ERB-1, ITQ-1, ITQ-2, MCM-36, MCM-49, MCM-56, and UZM-8.

6. The process of claim 4, wherein the zeolite is selected from the group consisting of MCM-22, PSH-3, SSZ-25, ERB-1, ITQ-1, ITQ-2, MCM-36, MCM-49, MCM-56 and UZM-8.

7. The process of claim 1, wherein the alkylating (a) is conducted under conditions such that at least part of the benzene is in the liquid phase.

8. A process for producing styrene, the process comprising:
    (a) alkylating benzene with ethylene to produce ethylbenzene and polyethylated benzenes;
    (b) transalkylating at least some of the polyethylated benzenes from (a) with benzene to produce additional ethylbenzene;
    (c) dehydrogenating at least some of the ethylbenzene from (a) and (b) to produce a dehydrogenation effluent comprising styrene, together with benzene and toluene as by-products;
    (d) separating a fraction containing benzene, toluene and water from the dehydrogenation effluent without prior fractionation to remove the toluene, wherein said fraction contains in excess of 2 ppm by weight of basic nitrogen impurities;
    (e) passing at least part of the benzene, toluene and water-containing fraction through a bed of an adsorbent comprising at least one of an acidic clay, and an acidic ion exchange resin to remove basic nitrogenous impurities therefrom and produce a purified benzene, toluene and water-containing fraction containing less than 50 ppb by weight of basic nitrogen impurities; and
    (f) recycling a purified benzene-containing fraction to the alkylating (a) and/or the transalkylating (b).

* * * * *